United States Patent [19]

Coll

[11] 4,072,710
[45] Feb. 7, 1978

[54] PROCESS FOR PREPARING ACID CHLORIDES

[76] Inventor: Antonio Luis Palomo Coll, Maestro Perez Cabrero 7, Barcelona, Spain

[21] Appl. No.: 629,786

[22] Filed: Nov. 7, 1975

[30] Foreign Application Priority Data

Nov. 9, 1974 Spain .................................... 431806
Oct. 8, 1975 Spain .................................... 441581

[51] Int. Cl.$^2$ ............................................. C07C 51/58
[52] U.S. Cl. ............................ 260/544 D; 544/176; 260/192; 260/239.1; 260/239.3 D; 260/287 G; 260/295 R; 260/295.5 R; 260/307 A; 260/307 H; 260/332.2 C; 260/345.5; 260/349; 260/397.1; 260/465 R; 260/465.1; 260/544 L; 260/544 N; 260/544 S; 260/544 Y; 260/518 R; 560/82; 560/43

[58] Field of Search .......... 260/544 Y, 544 L, 544 D, 260/192, 307 H, 295.5, 287 G, 347.3, 239.1, 345.7, 397.1, 465 R, 465.1, 544 S, 544 N, 332.2 A, 307 A, 345.5, 349, 295 R, 475 SC, 247.2 A, 347.5, 239.3 D

[56] References Cited

U.S. PATENT DOCUMENTS

| | | | |
|---|---|---|---|
| 3,364,259 | 1/1968 | Scigliano ......................... | 260/544 D |
| 3,742,047 | 6/1973 | Prill .................................. | 260/544 Y |
| 3,758,569 | 9/1973 | Bissing et al. .................... | 260/544 Y |
| 3,763,250 | 10/1973 | Rai et al. .......................... | 260/544 Y |
| 3,803,199 | 4/1974 | Voss et al. ........................ | 260/543 F |
| 3,829,477 | 8/1974 | Strini ................................ | 260/544 Y |

*Primary Examiner*—Norman Morganstern
*Attorney, Agent, or Firm*—Haseltine, Lake & Waters

[57] ABSTRACT

A process for preparing acid chlorides, wherein a silyl ester having an aliphatic, aromatic, alkanoaromatic or heterocyclic group which may support substituents, and having a low molecular weight alkyl or phenyl group is reacted with thionyl chloride in an inert solvent at a temperature of from −15° to 50° C, preferably from 10° to 50° C.

6 Claims, No Drawings

PROCESS FOR PREPARING ACID CHLORIDES

FIELD OF THE INVENTION

The present invention relates to a process for preparing acid chlorides, particularly for their use in acylation processes for the preparation of amides, hydrazides, esters, etc.

DESCRIPTION OF PRIOR ART

The technical literature contains descriptions of numerous methods for the preparation of acid chlorides, consisting mainly in the treatment of an acid with excess quantities of halogenating agents. This leads to extended treatment times and high operating temperatures with many acids giving low conversion yields, while others remain unaltered or decompose immediately.

It is known that silyl esters are readily alterable by hydroxyl agents such as ambient moisture and alcohols, which makes them hard to preserve, whereby they have to be prepared just prior to their conversion by halogenating agents.

They may be prepared by methods described in the literature which use products such as N-methyl-trimethylsilylacetamide, diethyl-trimethyl-phosphorimidates, hexamethyldisilazane as silylating agents or mixtures thereof with trimethylchlorosilane and trimethylchlorosilane itself, the latter being particularly useful with acid alkali salts.

The literature contains numerous references to the difficulty in preparing acidochlorides, such as the decarboxylation and degradation undergone by phenylmalonic acids, their carboxyesters and carboxyamides, all of which is overcome by the present process.

There are also important difficulties affecting the purity and yield in the preparation of acid chlorides of cyano-carboxylic compounds, because of the hydrogen chloride released, as well as the well known decarboxylation. Thus, for example, the maximum yield with cyanacetic acid is 54% and the product is recommended for immediate use since, even when stored at low temperatures, it undergoes alteration (A. Weissberger and H.D. Porter; J. Am. Chem. Soc. 65, 52 (1943).

SUMMARY OF THE INVENTION

The present new process comprises reacting a silyl ester of an acid with thionyl chloride at room temperature or refluxing a solution of the silyl ester in methylene chloride, for periods of from 15 to 60 minutes, according to the temperature. The conversion is performed with approximately stoichiometric amounts of the silyl ester and halogenating agent.

All silyl esters are appropriate for the process, with no limitations nor the formation of acid anhydrides having occurred. This latter, which leads to the loss of exactly half the acid converted into anhydride in an acylation process, occurs in conventional methods for the preparation of acid chlorides.

Silyl esters may be prepared by using bis-trimethylsilylacetamide or bis-trimethylsilylformamide may also be used, nevertheless, the product affording optimum results for the purposes of the invention is N-trimethylsilyl-2-oxazolidinone (TMSO), since silyl ester solutions are obtained in short times (5 to 15 minutes) at room temperature. This agent is a cheap product used in the process in almost stoichiometric amounts, depending on the degree of moisture in the acids and solvents. Silyl esters may be formed with TMSO in numerous solvents, such as: acetonitrile, chloroform, benzene, 1,2-dimethoxyethane, 1,2-dichloroethane, dimethylacetamide, dimethylformamide, etc. preferably methylene chloride, acetonitrile and 1,2-dichloroethane, although in the majority of the examples to be described hereinafter, reference is made to methylene chloride in view of its low boiling point and easy recovery.

It has also been shown now that a similar conversion takes place between a trimethylsilyl ester and thionyl chloride as per the stoichiometry of the following reaction:

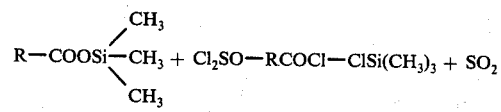

and, also, it may be specifically controlled, only the silyl ester being converted, in the presence of a trimethylsilyl sulphonylester.

In accordance with the above scheme, it is possible to recover the trimethylchlorosilane with controlled distillation and, when thionyl bromide or thionyl fluoride are used, the corresponding halosilane is obtained, the result being the acid bromide or fluoride. Table I gives the results obtained with a series of acids according to the above reaction.

TABLE I

| ACID (1 cmole) | SILYLATION REACTANT (x) | HALOGENATING REACTANT (ml) | | HALIDE FORMED | THEORETICAL % |
|---|---|---|---|---|---|
| 3,5-dinitrobenzoic | BSA | $SOBr_2$ | (1) | Bromide | 98,7 |
| 2,6 dimethoxybenzoic | TEA/TMCS | $SOCl_2$ | (1) | Chloride | 99,8 |
| Phenylmalonic | TMSO | $SOCl_2$ | (2) | Dichloride | 99,7 |
| 3,4,5-trimethoxy-benzoic | HMDS | $SOBr_2$ | (1) | Bromide | 96,4 |
| 2,6-dichlorobenzoic | TEA/TMCS | $SOBr_2$ | (1) | Bromide | 95,6 |
| Mandelic | TMSDEA/TMSO | $SOCl_2$ | (1) | Chloride | 99,2 |
| Diethylaminoacetic | BSU | $SOCl_2$ | (1) | Chloride | 93,4 |
| Thienyl-2-malonic | TMSO | $SOF_2$ | (2) | Difluoride | 99,6 |
| O-toluic | TEA/TMCS | $COCl_2$ | (1) | Chloride | 97,2 |
| Fumaric | TMSO | $SOCl_2$ | (2) | Dichloride | 98,9 |
| Lauric | TMSO | $SOCl_2$ | (1) | Chloride | 99,8 |
| Undecylenic | TMSO | $SOCl_2$ | (1) | Chloride | 99,5 |
| Oleic | TMSO | $SOCl_2$ | (1) | Chloride | 98,5 |
| Succinic | TMSO | $SOCl_2$ | (2) | Dichloride | 99,2 |
| Succinic | TMSO | $SOCl_2$ | (1) | Mono-chloride | 88,7 |
| Thienylacetic | TEA/TMSO | $SOCl_2$ | (1) | Chloride | 99,3 |

(x) The abbreviations used are the usual ones for these reactants. The experimental technique corresponds to that of the illustrative examples.

This circumstance makes for a cheaper process, since these halosilane may be recycled to obtain trimethylsilyl esters, either directly through the halosilane or indirectly through the preparation of other silylating reactants such as, for example, TMSO, described in U.S. Patent application Ser. No. 443,849.

If bis-trimethylsilylesters are formed with thionyl chloride, the acid chloride in the carboxyl function is obtained with sulphocarboxylic compounds. This advantage allows the preparation of derivatives with the free sulphonic function, as is the case of the alpha-sulphophenylacetic, sulphobenzoic, sulphofuroic and sulphosalicylic acids, from which it is now possible to obtain new combinations of the sulphonic group, which is thereafter easily unblicked, using simple technology.

Isoxazolyl and quinolinecarboxylic acids are also quickly converted into their chlorides. In a similar way so are glycirrhetic, cholic and chromeno-2-carboxylic acids. The last named does not produce the formation of chlorinated compounds in the nucleus, which are originated by the direct action of the thionyl chloride, a fact known to experts in this field (G.P. Ellis and G. Barker. Progress in Medicinal Chemistry, Butterworths, London, 1972. Vol. 9 (1) p. 65).

In the case of alpha-nitro acids, decarboxylation is so rapid that it has not been possible to prepare their chlorides, nevertheless, stabilisation as silyl esters and reaction with thionyl chloride provides solutions ready for use.

Preferred silyl esters are the trimethylsilyl esters since the silylation reactants derived from the trimethylsilyl group are much cheaper, although esters formed from low molecular weight alkyls and phenyls may also be used. As halogenating agent, apart from carbonyl chloride, from among the thionyl halides thionyl chloride is preferred to the thionyl fluorides and bromides, since it is a low cost commercial product easily obtainable on the market.

The Examples, in certain cases, describe the preparation of derivatives of the chlorides and, in other cases, they are identified by their IR spectrum, the typical high intensity band showing in the region of 1740–1780 cm$^{-1}$. A solution of benzoic acid derivatives in carbon tetrachloride gives two readings.

Since the importance of acid chlorides for the preparation of derivatives, particularly penicillins and cephalosporins, is known, an important aspect of this invention is that the process described produces acid chloride solutions which may be used directly, without requiring prior isolation.

It is known that numerous acids do not react under moderate conditions with the thionyl halides in almost stoichiometric proportions. It is also known that no carboxylic acid ester can form an acid halide with the thionyl halides. Therefore, the results described in the present invention must be considered to be surprising and of great value in modern acylation process technology and which are importantly applicable in the synthesis of antibiotics of the penicillin and cephalosporin group, as also in the field of the sulpha drugs (Hypoglycemic and chemotherapeutical) and depressors of the benzoazepinone group, among many other examples that could be cited.

DETAILED DESCRIPTION OF THE INVENTION

A series of examples of the present invention are described. In view of their merely illustrative nature, these examples must be considered as devoid of any limitative effect with respect to the scope of legal protection applied for.

EXAMPLE I

A solution of alpha-chlorophenylacetic acid silyl ester was prepared with 5 cmole acid (8.52 g) in methylene chloride (25 ml), triethylamine (0.25 ml) and 3-trimethylsilyl-2-oxazolidinone (TMSO) (6.2 cmole, about 10 ml) and the mixture was stirred for 15 minutes at room temperature (20° C). Thereafter thionyl chloride (7 ml; 9.8 cmole) was added and stirring was continued for 30 minutes at room temperature. Thereafter the solvent is evaporated at reduced pressure (r.p.) and the remaining oil is treated with a mixture of n-heptane (25 ml) and ethyl acetate (20 ml), whilst stirring and cooling. The precipitated 2-oxazolidinone (4 g) is filtered off. The solvent is removed by evaporation and then the filtrate is distilled under vacuum to give pure alpha-chlorophenylacetyl chloride (8.7 g; Y = 92%). It gives a characteristic band in the IR spectrum at about 1,800 cm$^{-1}$.

EXAMPLE II

A solution of D,L-alpha-azidophenylacetic acid trimethylsilyl ester was prepared with 1 cmole acid (1,771 g), methylene chloride (10 ml), triethylamine (1 mmole; 0.14 ml) and TMSO (2.1 ml) and the mixture was stirred for 15 minutes at room temperature. Thereafter thionyl chloride (1.4 cmole; 1 ml) was added and the mixture was heated for 15 minutes with reflux; thereafter the solvent was removed by evaporation at reduced pressure and the remaining oil was redissolved in methylene chloride (10 ml) to give a solution of alpha-azidophenylacetyl chloride.

The above solution was cooled and there was added thereto a solution of aniline (3.0 cmole; 2,79 g) in methylene chloride (5 ml). The mixture was stirred for 15 minutes and water (10 ml) and hydrochloric acid to Ph = 1 were added; the organic phase is decanted off and the solvent is removed by evaporation. After treatment with sodium bicarbonate, the residue gives the anilide with a virtually quantitative yield, m.p. = 84°–7° C (ethanol-n-hexane).

EXAMPLE III

TMSO (2 ml) is added to a suspension of 3-(2,chlorophenyl)-5, methyl-4-isoxazolylcarboxylic acid (1 cmole; 2.376 g) in methylene chloride (10 ml) and triethylamine (1 mmole; 0.14 ml), with stirring at room temperature (20° C) to give a solution. After further stirring for 10 minutes, there is added thionyl chloride (1.1 cmole; 0.83 ml), with stirring being continued for a further 60 minutes at 20° C. An acid chloride solution is produced from which, after treatment with aniline (3.2 cmole; 3,0 g) in methylene chloride and then with water-hydrochloric acid, the anilide (3.12 g) is isolated with a quantitative yield m.p. 193°–4° C (ethanol).

EXAMPLE IV

To a suspension of 1 cmole of 2,6-dinitrobenzoic acid (2.121 g) in methylene chloride (10 ml), there is added triethylamine (0.14 ml) and TMSO (2.10 ml) to give a solution of the silyl ester to which thionyl chloride (1.4 cmole; 1 ml) is added with heating thereafter under reflux for 15 minutes. The solvent is removed with evaporation and the residue is redissolved in methylene chloride (10 ml) to give an acid chloride solution.

Aniline (3 ml) in methylene chloride (10 ml) is added to the above solution and after 15 minutes water-hydrochloric acid is added, the solution is filtered, washed with water and dried to give 2,6-dinitroanilide (2.90'g) with a quantitative yield; only slightly soluble in ethanol. The functional groups are identified by their IR spectrum.

EXAMPLE V

Following Example 4 and using 3,5-dinitrobenzoic acid instead of 2,6-dinitrobenzoic acid, the result is an acid chloride giving a reading on the IR spectrum. With aniline, it gives anilide with m.p. 237°–7° C and similar yield.

EXAMPLE VI

Following Example 4 and using 2,6-dimethoxybenzoic acid (1 cmole; 1,820 g) instead of 2,6-dinitrobenzoic acid, the result is a solution of the acid chloride, to which ethanol is added (2 cmole; 0.92 g). After evaporation of the solvent and washing with water, the ethyl ester is isolated (1.93 g; Y = 99.0%) with m.p. 68°–69° C (ethanol).

EXAMPLE VII

According to Example 1 and if benzoic acid is used instead of alpha-chlorophenylacetic acid, the result is benzoyl chloride with a quantitative result.

EXAMPLE VIII

According to Example 1 and if trichloroacetic acid is used instead of alpha-chlorophenylacetic acid, the result is the acid chloride with a quantitative result (m.p. = 115°–119° C).

EXAMPLE IX

The disilyl compound of salicylic acid is prepared with 1 cmole of acid (1.380 g) in chloroform, triethylamine (0.1 ml) and TMSO (4.2 ml) with stirring for 30 minutes. Thionyl chloride (1.4 cmole; 1 ml) is added and after stirring for 60 minutes at 20° C, the result is an acid chloride solution. If this solution is cooled to −10° C and treated with o-toluidine (in methylene chloride), the resulting product is the amide (1.109 g with a yield of 97.7%) with m.p. = 147°–8° C (benzene).

EXAMPLE X

To a suspension of 0.1 mole of N(1-methyl-2-ethoxy-carbonylvinyl)-D-alpha aminophenylacetic acid potassium salt (31.04 g) in 1,2-dimethoxyethane (50 ml), with stirring in an ice-water bath, there is added 0.3 mole of trimethylchlorosilane and then, slowly, triethylamine to pH = 7.0. The solution is filtered under an inert atmosphere and 0.1 mole of thionyl chloride (8.0 ml) is added with stirring for 60 minutes at 20° C to give an acid chloride solution.

The acid chloride is obtained in a similar way using N-(1-methyl-2-ethoxycarbonyl-vinyl)-p-hydroxi-alpha-aminophenylacetic acid.

EXAMPLE XI

A suspension of 0.1 mole of p-nitrobenzoic acid (16.7 g) in methylene chloride (100 ml) is stirred with triethylamine (1.4 ml) and TMSO (22 ml) at 20° C to give a solution to which thionyl chloride (0.14 mole; 10 ml) is added followed by heating under reflux for 15 minutes. Then the solvent is distilled off with the slight excess of thionyl chloride. The residue is dissolved in methylene chloride (50 ml) to give an acid chloride solution. A weighed sample of the solution, with aniline, gives the anilide with m.p. 206°–9° C and a quantitative yield.

EXAMPLE XII

A solution of nicotinic acid (1 cmole; 1.231 g) in methylene chloride with triethylamine and TMSO is treated with thionyl chloride (1.1 cmole; 0.8 ml) and heated under reflux for 15 minutes to give an acid chloride solution. In a similar way the corresponding acid chloride is obtained with 4-pyridincarboxilic acid.

EXAMPLE XIII

A solution of isocinchomeronic acid silyl monoester, prepared with 0.1 mole of acid (16.7 g) in xylene (100 ml) is heated under reflux for 60 minutes, thereafter it is cooled and 0.14 mole of thionyl chloride (8.0 ml) is added, followed by heating for 15 minutes at 45° C to give a nicotinic acid chloride solution.

EXAMPLE XIV

When a suspension of glycin 2-methylamino-5-chlorobenzophenone (1 cmole; 3.028 g) is treated as in Example 2, the intermediate acid chloride forms the cyclic amide and gives 7-chloro-1-methyl-5-phenyl-1,2-dihydro-3H-1,4-benzodiazepin-4-one (2.711 g; Y = 95.2%). In a similar way the 7-nitro derivative is obtained, using glycin 2-methylamino-5-nitrobenzophenone.

EXAMPLE XV

A suspension of 5-chlorosalicylic acid (1 cmole; 1.725 g) in methylene chloride, treated as per Example 10, gives an acid chloride solution with similar yield.

EXAMPLE XVI

A suspension of 5-indanyl-phenylmalonic acid halfester (1 cmole; 2.963 g) in benzene (10 ml), triethylamine (0.14 ml) and TMSO (2.2 ml), when stirred at 20° C gives a silyl ester solution which, when treated with thionyl chloride (1.4 cmole; 1 ml) with heating for 30 minutes at 40° C gives an acid chloride solution. With aniline it forms the anilide insoluble in butanol. The IR spectrum shows the readings corresponding to the amide and ester functions.

EXAMPLE XVII

If the halfester of the previous example is replaced by halfamide, phenylmalonic acid morpholide (1 cmole; 2.492 g) the result is the corresponding acid chloride solution.

EXAMPLE XVIII

A suspension of disodium phenylmalonate (1 cmole; 2.41 g) in benzene (25 ml) and trimethylchlorosilane (2.3 cmole; 3.08 ml) gives a solution of the silyl diester which, filtered with sodium chloride and treated with thionyl chloride (0.90 cmole; 0.64 ml) with heating to 50° C, gives a monosilyl ester phenylmalonate halfchloride solution. In a similar way, if 2 cmoles of thionyl chloride are used, the result is a solution of phenylmalonic acid dichloride.

EXAMPLE XIX

A suspension of alpha-(2,6-dinitrobenzoylamino)-phenylacetic acid (1 cmole; 3.452 g) in methylene chloride (15 ml), triethylamine (0.14 ml) and TMSO (4.4 ml) gives a solution which, after 15 minutes, is treated with thionyl chloride (1.4 cmole; 1 ml) and heated under reflux for 15 minutes to give the acid chloride with a virtually quantitative yield.

EXAMPLE XX

Following Example 4 and replacing the 2,6-dinitrobenzoic acid with 3,4,5-trimethoxybenzoic acid (1 cmole; 2.122 g) and the methylene chloride with dimethylacetamide, the acid chloride solution is prepared with similar yield.

EXAMPLE XXI

Following Example 4 and replacing the 2,6-dinitrobenzoic acid with 2,6-dichlorobenzoic acid (1 cmole; 1.910 g) the result is a similar yield of the acid chloride in solution.

EXAMPLE XXII

Following Example 10 and replacing the salicylic acid with mandelic acid (1 cmole; 1.521 g) the result is a solution of the corresponding acid chloride which, when treated with ammonia gives mandelamide.

EXAMPLE XXIII

A suspension of alpha-nitrophenylacetic acid disodium salt (1 cmole; 2.251 g) treated as in Example 19, gives a solution of the corresponding acid chloride.

EXAMPLE XXIV

To a solution of the trimethylsilyl ester, prepared from alpha-(hexamethylene-tetramine) phenylacetic acid (1 cmole; 3.107 g), methylene chloride (15 ml), triethylamine (0.1 ml) and TMSO (2.1 ml), there is added thionyl chloride (1.4 cmole; 1 ml) and after heating for 15 minutes under reflux, the result is a solution of the acid chloride.

EXAMPLE XXV

A solution of the trimethylsilyl ester of 5-nitro-2-furoic acid (1 cmole; 1.570 g) is prepared according to Example 4 and after heating the mixture with thionyl chloride under reflux for 15 minutes, the result is a solution of the acid chloride.

EXAMPLE XXVI

A suspension of sodium benzylidenecarbazate (1 cmole; 1.861 g) in methylene chloride, treated with trimethylchlorosilane, according to Example 19, gives a solution of the corresponding acid chloride.

EXAMPLE XXVII

A solution of diethylaminoacetic acid trimethylsilyl ester (1 cmole; 1.311 g) prepared with the acid and TMSO and treated with thionyl chloride according to Example 1 gives the acid chloride.

EXAMPLE XXVIII

Example 1 is followed and the alpha-chlorophenylacetic acid is replaced with 5 cmoles of 6-(acylamino)-penicillinic acid, prepared by sodium salt extraction at pH = 2 with methylene chloride. The trimethylsilyl ester obtained is treated with thionyl chloride and gives a solution of the corresponding penicillanic acid chloride. When D(−)alpha-azidobenzylpenicillin is used, the result is the acid chloride, identified by its IR spectrum. With penoxymethyl penicillin, a solution of the acid chloride in benzyl alcohol gives the benzyl ester with m.p. = 75°–76° C and $[\alpha]_D^{25} = +144°$ (C1% acetone).

EXAMPLE XXIX

Example 1 is followed and the alpha-chlorophenylacetic acid is replaced with 5 cmoles of 7(acylamino)-desacetoxycephalosporanic acid, prepared by extraction of the sodium salt at pH = 2 with methylene chloride. The trimethylsilyl ester obtained is treated with thionyl chloride and gives a solution of the corresponding acid chloride. With the D(−)-alpha-azidophenylacetyl derivative, it gives the acid chloride identified by its IR spectrum.

EXAMPLE XXX

Methylene chloride (10 ml) is added to 1 cmole (1.901 g) of chromeno-2-carboxylic or 4-oxo-4H-1-benzopiran-2-carboxylic acid followed by n-ethylpiperidine and TMSO (2 ml); after stirring at room temperature for 15 minutes, there is added thionyl chloride (1 ml) and the mixture is heated for 15 minutes at 45° C to give a solution of the corresponding acid chloride with a virtually quantitative yield.

EXAMPLE XXXI

Following the previous example and replacing the chromeno-2-carboxylic acid with desoxycholic acid (3.920 g), the result is a solution of the corresponding acid chloride.

EXAMPLE XXXII

TMSO (2.2 ml) is added to the suspension of 1 cmole (4.085 g) of cholic acid in methylene chloride (15 ml) and 1 mmole of triethylamine (TEA); after 10 minutes thionyl chloride (1 ml) is added in one amount and the mixture is stirred for 60 minutes at 20° C to give a solution of the corresponding acid chloride.

EXAMPLE XXXIII

Following the previous Example and replacing the cholic acid with 1 cmole of glycirrhetic acid (4.706 g), the result is a solution of the corresponding acid chloride with excellent yield.

EXAMPLE XXXIV

A suspension of 1 cmole (3.452 g) of alpha-(2,6-dinitrobenzoylamino)-phenylacetic acid, in benzene (10 ml) with n-ethylpiperidine (0.15 ml) and TMSO (2.2 ml) gives a silyl ester solution, to which thionyl chloride (1 ml) is added; after stirring for 30 minutes at 20° C, first the acid chloride is produced which, is cycled and gives the corresponding oxazolone with a yield of 98.5% of theory.

EXAMPLE XXXV

Methylene chloride is added to 1 cmole (3.404 g) of N-(2-methylamino-5-chloro-alpha-phenyl-benzylidene) glycin-N-oxide trimethylsilyl ester. Thereafter, thionyl bromide (0.7 ml) is added and after 15 minutes stirring at room temperature the result is the corresponding bromide. If stirring is continued for a further 15 minutes, cyclization takes place to give 7-chloro-5-phenyl-1,3-dihydro-3H-1,4-benzodiazepin-2-one-N-oxide with almost quantitative yield.

EXAMPLE XXXVI

Following the previous Example and replacing the glycin derivative with N-[2-o-trifluoromethyl-phenylamino)-5-chloro-alpha-methylbenzylidene] glycin trimethylsilyl ester, the result is the corresponding acid bromide. With extended stirring cyclization takes place to give the 1,4-benzodiazepin-2-one derivative, with similar yield.

EXAMPLE XXXVII

Methylene chloride (10 ml.) and thionyl chloride are added to N (malonyl)-4-nitro-2-phenylamino-aniline trimethylsilyl ester (3.874 g). Stirring at room temperature gives the acid chloride. If further stirred, cyclization takes place and gives 1,5-benzodiazepin-4-one, with virtually quantitative yield.

EXAMPLE XXXVIII

TMSO (5 ml) and triethylamine (0.3 ml) is added to 0.02 mole (8.00 g) of alpha-carboxy-benzylpenicillin monosodium salt in methylene chloride (40 ml) at −5° C and stirring is continued for 30 minutes. Thereafter thionyl chloride (2 ml) is added with stirring at the same temperature for 120 minutes to give a solution of alpha-chlorocarbonyl-benzylpenicillin. 5-indanol is added, the mixture is stirred for 4 hours, extracted with water at pH = 2, the organic phase is washed, dried, and sodium 2-ethylhexanoate is added to pH = 6.5. The mixture is diluted with isopropanol, allowed to rest for 48 hours at 5° C, filtered and washed to give 9.06 g (87.5%) of alpha-carboxy-indanyl-benzyl penicillin.

EXAMPLE XXXIX

Following the previous Example, alpha-chlorocarbonyl-benzylpenicillin is obtained and if the 5-indanol is replaced by phenol, the result is alpha-carboxy-benzyl-penicillin.

EXAMPLE XL

To a solution of phenylmalonic trimethylsilyl ester prepared with 0.1 mole of the acid (18.0) and bisilylacetamide in chlorobenzene (100 ml), there is added thionyl chloride (10 ml) with stirring being maintained at room temperature (20°) for 60 minutes. Thereafter the mixture is distilled at ordinary pressure to draw off trimethylchlorosilane (13.0 ml) and the resulting solution gives trimethylsilyl alpha-chlorocarbonyl-phenylacetate. Thereafter phenol (15.0 g) is added and stirring is continued at 45° C for 8 hours. The mixture is then washed with water and the pH is adjusted to 7.0 with sodium bicarbonate solution. The water phase is decanted off and the pH is adjusted to 5.0 with hydrochloric acid. The phenylmalonic acid phenyl monoester precipitates out, yield 95%, m.p. 105°–110°(d) and when recrystallised from benzene-n-hexane, has m.p. 116°–118° (d).

EXAMPLE XLI

When a suspension of 0.1 mole (25.6 g) of phenylmalonic acid phenyl monoester in benzene (100 ml) is mixed with TMSO and triethylamine (0.01 mole), the result is a solution of the trimethylsilyl ester and a precipitate of 2-oxazolodinone with is isolated by filtration. Thereafter thionyl chloride (10 ml) is added. The mixture is heated for 15 minutes at 40° and then distilled at the same temperature and reduced pressure. Trimethylchlorosilane is drawn off (12.5 ml) to leave a solution of phenyl alpha-chlorocarbonylphenylacetate with a practically quantitative yield. This solution, added over a solution of 0.1 mole of 6-amino-penicillanic acid in the triethylamine salt form, in methylene chloride, produces alpha-carboxyphenyl-benzylpenicillin, which is isolated by the usual methods in the sodium salt form.

EXAMPLE XLII

A solution of alpha-sulphophenylacetic acid, 1 cmole (2.161 g free from ether of solvation), 1,2-dimethoxyethane (15 ml), with TMSO (4.4 ml) and triethylamine as catalyst (a few drops) is stirred to produce a disilyl ester solution. The precipitated 2-oxazolidinone is removed by filtering and thionyl chloride (1 ml) is added to the liquids. The mixture is then heated for 15 minutes at 45° to give a solution of alpha-trimethylsilylylsulphonylphenylacetic acid chloride, with a virtually quantitative yield. Trimethylchlorosilane is isolated from the above solution by distillation at reduced pressure.

EXAMPLE XLIII

Following the previous Example and replacing the alpha-sulphophenylacetic acid with 1 cmole (2.161 g) of p-sulphophenylacetic acid and the 1,2-dimethoxyethane with 1,2-dichloroethane, the result is a solution of p-trimethylsilylylsulphonylphenylacetic acid chloride, with similar yield.

EXAMPLE XLIV

A suspension of 4-chloro-5-sulphosalicylic acid, (1 cmole, 2.526 g) in toluene (15 ml), heated first with trimethylsilyldiethylamine (1 cmole) and then with HMDS (2 cmole) under reflux gives the trimethylsilyl compound derived in the three functions. Thereafter thionyl chloride (1 ml) is added and the mixture is heated at 45° for 15 minutes to give a solution of the corresponding acid chloride, with a practically quantitative yield.

EXAMPLE XLV

Following the previous Example and replacing the 4-chloro-5-sulphoxalicylic acid with sulphosalicylic acid (with water of crystallisation) and the toluene with acetonitrile, the result is a solution of the corresponding acid chloride.

EXAMPLE XLVI

A suspension of 1 cmole (1.670 g) of 8-quinoline carboxylic acid in carbon tetrachloride (16 ml), with TMSO (2.2 ml) and triethylamine (0.02 ml) with stirring at room temperature produces a solution of trimethylsilyl ester. The precipitated 2-oxazolidinone is filtered out and thionyl chloride (1 ml) is added to the solution; thereafter it is heated for 20 minutes at 45° C to give a solution of the corresponding acid chloride with almost quantitative yield.

EXAMPLE XLVII

Following the previous Example and replacing the 8-quinoline carboxylic acid with 5-methyl-isoxazolyl-2-carboxylic acid, the result is a solution of the corresponding acid chloride with similar yield.

EXAMPLE XLVIII

Thionyl chloride (1 ml) is added to a solution of nitro-acetic acid trimethylsilyl ester prepared with 1 cmole of acid (1.050 g) in methylene chloride (10 ml) with TMSO (2.1 ml) and triethylamine (0.01 ml), the solution is heated for 15 minutes at 40°–45° and gives a solution of the corresponding acid chloride with quantitative yield.

EXAMPLE XLIX

Following the previous Example and replacing the nitroacetic acid with alpha-nitrophenylacetic acid sodium salt (2.251 g) and the TMSO with trimethylchlorosilane, the result is a solution of the silyl ester and a sodium chloride precipitate. The solution is filtered and reacted with thionyl chloride to give the corresponding acid chloride with excellent yield.

EXAMPLE L

Following Example 41 and replacing the phenol with p-chlorophenol, the p-chlorophenyl phenylmalonate halfester is isolated with m.p. = 118°–122° C (d); recrystallised in benzene, m.p. = 122.5°–124° (d).

EXAMPLE LI

Following Example 41 and replacing the phenol with 5-indanol, the 5-indanol phenylmalonate halfester is isolated with similar yield. Purified by recrystallisation at the rate of 4.5 g per 10 ml benzene, it is cooled, filtered and washed with benzene and n-heptane to give 3.67 g with m.p. 105°–7° (d) (some softening at 95°).

EXAMPLE LII

Following Example 41 and replacing the phenylmalonic acid with thienyl malonic acid, the phenyl thienylmalonate halfester is isolated with similar yield, with m.p. 90°–93° (d).

EXAMPLE LIII

Following Example 41 and replacing the phenylmalonic acid with furylmalonic acid and the phenol with ethanol, the ethyl furylmalonate halfester is isolated with similar yield. This is an oil insoluble in water and soluble in methylene chloride. Decomposes with heating to give ethyl 2-furylacetate.

EXAMPLE LIV

Following Example 41 and replacing the phenol with 2-hydroxynaphthalene, the 2-naphthyl phenylmalonate halfester is isolated with similar yield, with m.p. = 130°–133°.

EXAMPLE LV

To 1 cmole of prostaglandine, with carboxyl function, there is added methylene chloride (10 ml) with a catalytic amount of diethylamine, followed by TMSO with stirring for 15 minutes. The trymethylsilyl ester solution is heated under reduced pressure to evaporate the amine. Thereafter 1 ml of thionyl chloride is added with stirring for 45 minutes at room temperature to give a solution of the acid chloride. When reacted with alcohols, amines and hydrazines, this solution respectively gives esters, amides and hydrazides, which are isolated by evaporation of the solvent.

What I claim is:

1. A process for the preparation of acid chlorides, wherein there is used a silyl ester of the following general formula:

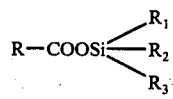

where R is a substituted or unsubstituted aralkyl, aliphatic, aromatic, or heterocyclic group provided that the substituent is not an amino group, and $R_1$, $R_2$ and $R_3$ are alkyl of 1–3 carbon atoms or phenyl, which is reacted with thionyl chloride in an inert solvent at a temperature of from −15° to 50° C to obtain a compound of the general formula:

R—COCl where R has the same meaning as given above.

2. A process for the preparation of acid chlorides, wherein an acid trimethylsilyl ester is reacted in a solvent with thionyl chloride at a temperature of between 10° and 50° C.

3. A process of claim 1, wherein the reaction between a silyl ester and thionyl chloride is conducted in an inert medium selected from the group of solvents consisting of methylene chloride, acetonitrile, chloroform, 1,2-dichloroethane, 1,2-dimethoxyethane, benzene, toluene, xylene, chlorobenzene, tetrahydrofurane, dioxane, chloroform, dichloroethylene, carbon tetrachloride, to obtain an acid chloride.

4. The process of claim 2, wherein the trimethylsilyl ester is obtained in a solvent by reaction of an acid with a silylating agent, and is thereafter reacted with thionyl chloride to obtain an acid chloride.

5. The process of claim 1, wherein an acid is reacted with a silylating reactant of the group consisting of trimethylchlorosilane, hexamethyldisilazane, bis-trimethylsilylacetamide, bis-silylurea, 3-tripropylsilylchlorosilane, butyldiethylchlorosilane, triphenylchlorosilane, silylphosphorimidates and bis-silylformamide, to obtain a compound of the following formula:

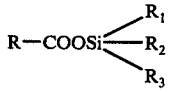

where R, $R_1$, $R_2$ and $R_3$ have the meaning given above, R being capable of supporting the substituents methyl, methoxy, nitro, cyano, carboxy, carboxyesters, carbamoyl, halogen, hydroxyl, thiol, sulphonic and sulphonamido, which is reacted with thionyl chloride to obtain a compound of the general formula:

RCOCl where R has the same meaning as given above.

6. A process for preparing α-chlorophenylacetyl chloride which comprises reacting α-chlorophenylacetic acid silyl ester with thionyl chloride in an inert solvent at about 20° C.

* * * * *